United States Patent [19]

Hestermann et al.

[11] 4,156,697

[45] May 29, 1979

[54] PRODUCTION OF ALKYLPHOSPHINES

[75] Inventors: Klaus Hestermann, Erftstadt-Bliesheim; Hartfrid Vollmer; Gero Heymer, both of Erftstadt-Liblar; Ernst-Günther Schlosser, Kalkheim, all of Fed. Rep. of Germany

[73] Assignee: Hoechst Aktiengesellschaft, Frankfurt am Main, Fed. Rep. of Germany

[21] Appl. No.: 823,140

[22] Filed: Aug. 9, 1977

[30] Foreign Application Priority Data

Aug. 13, 1976 [DE] Fed. Rep. of Germany ....... 2636558

[51] Int. Cl.² ............................................... C07F 9/50
[52] U.S. Cl. ........................ 260/606.5 P; 260/583 R; 260/583 J; 260/606.5 F; 423/358
[58] Field of Search .................... 260/606.5 P, 583 R, 260/583 J; 423/358

[56] References Cited

U.S. PATENT DOCUMENTS

| | | | |
|---|---|---|---|
| 2,437,797 | 3/1948 | Walling | 260/606.5 P |
| 3,153,670 | 10/1964 | Speziale et al. | 260/606.5 P X |
| 3,253,036 | 5/1966 | Crawford | 260/583 R X |
| 3,340,333 | 9/1967 | Baranauckas et al. | 260/606.5 P X |
| 3,366,687 | 1/1968 | Ellis et al. | 260/583 R |
| 3,760,001 | 9/1973 | Staendeke | 260/606.5 P |

OTHER PUBLICATIONS

Degering, An Outline of Organic Nitrogen Compounds, University Lithoprinters, Michigan, p. 213 (1945).

*Primary Examiner*—Helen M. S. Sneed
*Attorney, Agent, or Firm*—Connolly and Hutz

[57] ABSTRACT

Alkyl phosphines of the general formula:

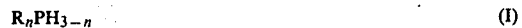

$$R_nPH_{3-n} \qquad (I)$$

are made. To this end hydrogen phosphide, a primary or a secondary phosphine is reacted with an alkylamine of the general formula:

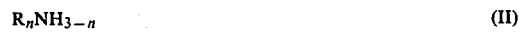

$$R_nNH_{3-n} \qquad (II)$$

in a molar ratio of 0.1 to 10 mols of the alkylamine of formula II per mol of hydrogen phosphide or primary or secondary phosphine. The reaction is effected at a 150° to 400° C., at atmospheric pressure or a superatmospheric pressure up to 1 atmosphere gauge, and in contact with a catalyst comprising active carbon, copper (II) chromite, or one or more metals of Group Ib or VIII of the Periodic System of the elements. The starting materials are passed through a reaction zone at a rate which permits a contact time between them and the catalyst of 0.1 to 400 seconds.

10 Claims, No Drawings

PRODUCTION OF ALKYLPHOSPHINES

This invention relates to a process for making alkyl phosphines of the general formula $R_nPH_{3-n}$, in which R stands for an alkyl group (identical or different alkyl groups can be present if there are more than one) having 1, 2 or 3 carbon atoms, and n is 1, 2 or 3.

A. W. Hoffman (Chem. Ber. 4, 605 (1871)) was the first to describe the preparation of alkyl phosphines by reacting an alkyl iodide RI with phosphonium iodide in the presence of ZnO: $2 \ RI + 2PH_4I + ZnO \rightarrow 2 \ RPH_2 \cdot HI + ZnI_2 + 2 \ H_2O$.

This process is, however, not satisfactory in respect of the following points: (1) it uses expensive iodides as starting materials; and (2) the reaction has to be effected discontinuously under high pressure in a closed vessel.

Alkyl phosphines are also obtainable by reacting an alkyl halide with an alkali metal or alkaline earth metal phosphide (cf. U.S. Pat. Specification No. 2,437,797, and R. I. Wagner, A. B. Burg, J. Am. Soc. 75, 3869 (1953)). To effect this reaction, however, it is necessary in a separate operation to initially produce the alkali metal or alkaline earth metal phosphide in liquid ammonia by the use of an elemental alkali or alkaline earth metal, which is difficult to handle.

In a process described more recently, a hydrocarbon halide is reacted with a complex of the formula $PH_3 \cdot AlCl_3$ (cf. F. Pass, E. Steininger, H. Zorn, Monatsb. Chemie 93, 230 (b 1962) and German Patent Specification ("Auslegeschrift") No. 1126867). To effect this reaction, it is necessary first to prepare in a separate operation the $AlCl_3$-complex of $PH_3$. In addition, $AlCl_3$ is consumed in the process just described.

A route which has often been tried for the preparation of alkyl phosphines on a laboratory scale comprises reducing an alkyl halogeno-phosphine by means of $LiAlH_4$ (cf. G. M. Kosolapoff, L. Maier, Organic Phosphorus Compounds, Wiley-Interscience, vol. 1, 4 (1972)). This process cannot for reasons of economy be used for the commercial production of organophosphines, as use is made therein of difficultly accessible alkyl halogenophosphines and of very expensive $LiAlH_4$.

Further processes have been described in the literature, which relate to the alkylation of yellow phosphorus by means of an alkyl iodide or alkanol (cf. Auger, V., C.R. Acad. Sci., Paris, 139, 639, 671 (1904); Kosolapoff, G. M., Organophosphorus Compounds, Wiley, (1950); Berthand, J., C.R. Acad. Sci., Paris 143, 1166 (1906)).

Disadvantages which have been encountered with these processes reside in the facts that the phosphines are obtained in minor yields only, and that the phosphines are additionally badly contaminated with various phosphine derivatives.

Further processes which should be mentioned describe the additive combination, initiated by means of free radicals, of $PH_3$ with olefins (cf. U.K. Patent Specification No. 673,451 and U.S. Patent Specification No. 2,604,094).

Apart from the fact that it is necessarily impossible in this manner to produce methyl phosphines, the various versions of this process suffer from the disadvantage that a large excess of $PH_3$ has to be used under pressure for making primary phosphines, which incidentally contain considerable quantities of secondary and tertiary phosphines as impurities.

In German Published Patent Specification ("Offenlegungsschrift") No. 2407461, it has been suggested that $PH_3$ should be reacted with an alkyl halide and converted into an alkyl phosphine by heterogeneous catalysis. This reaction entails the formation of quaternary phosphonium halides as by-products, which precipitate on the catalyst under the reaction conditions adopted, so that it is necessary for the catalyst to be frequently reactivated by elution.

U.S. Patent No. 3,389,183 describes a process for making long-chain tertiary phosphines having hydrocarbon radicals of 10 or more carbon atoms, wherein a long-chain primary phosphine is reacted with an alkyl iodide; by the use of the latter, however, the economy of the process is naturally greatly impaired.

Another process has been disclosed in U.S. Pat. No. 3,760,001, wherein elemental phosphorus is reacted with an alkyl halide in contact with an active carbon catalyst. Characteristic of this process, however, is the production of alkyl halogeno-phosphines (cf. German Patent Specification No. 1568928), alkyl phosphines being obtained as by-products only in insignificant proportions. Needless to say this is disadvantageous.

It is therefore an object of the present invention to provide a process permitting short-chain alkyl phosphines to be made from readily accessible starting materials, the process also being easy to carry out continuously.

According to the present invention, we provide a process for making an alkyl phosphine of the general formula:

$$R_nPH_{3-n} \qquad (I)$$

in which R stands for an alkyl group having 1, 2 or 3 carbon atoms and n is 1, 2 or 3, which comprises reacting hydrogen phosphide, a primary phosphine of the formula $RPH_2$ or a secondary phosphine of the formula $R_2PH$ with an alkylamine of the general formula $$R_nNH_{3-n} \qquad (II)$$

in which R and n have the meanings given above, in a molar ratio of 0.1 to 10 mols of the alkylamine of formula II per mol of hydrogen phosphide or primary or secondary phosphine; the reaction being effected at a temperature of 150° to 400° C., at atmospheric pressure or a superatmospheric pressure up to 1 atmosphere gauge, and with the exclusion of oxygen; a catalyst being employed comprising active carbon, copper (II) chromite, or one or more metals of Group Ib or VIII of the Periodic System of the elements, in free metal or phosphide form, deposited individually or in combination on a catalyst carrier; and the starting materials being passed through a reaction zone at a rate which permits a contact time between them and the catalyst of 0.1 to 400 seconds.

It is preferable to effect the reaction at a temperature of 250° to 350° C. The reaction may be effected in either a fixed bed reactor or a fluidized bed reactor. Use should preferably be made of a catalyst having a particle size of 0.5 to 10 mm for a fixed bed reactor, and use should preferably be made of a catalyst having a particle size of 40 to 200 microns for a fluidized bed reactor. In those cases in which an active carbon catalyst is employed, it can be any of the commercially available active carbons, but it is preferable for it to have a BET surface area of more than 10 m²/g. When the catalyst comprises one or more metals belonging to Group Ib or VIII of the Periodic System of the elements, the said metal(s) preferably comprise(s) one or more of the following: copper, iron, cobalt, nickel, rhodium, palladium, platinum. The catalyst carriers on which these metals are deposited can be the usual carriers having a large specific surface area. As indicated below (cf. Examples 12–17), these metal catalysts may function in phosphide form rather than in free metal form.

Further preferred features of the present process provide for the starting materials to be intimately mixed together, to be heated to reaction temperature and to be then contacted with the catalyst; and/or for the starting materials to be passed through the reaction zone at a rate which permits a contact time between them and the catalyst of 0.5 to 10 seconds.

The reaction of $PH_3$ or a primary or secondary phosphine with an alkylamine has not been described heretofore.

The catalysts which are employed in the present process can comprise commercially available materials, and in the case of the metallic catalysts they can be products prepared for use as hydrogenation catalysts; the latter are liable to be converted into metal phosphides by $PH_3$ immediately after the start of the reaction.

As already mentioned above, we use 0.1 to 10 mols of alkyl amine per mol of hydrogen phosphide or primary or secondary phosphine. In order to alkylate the phosphines to the desired stage as completely as possible, it is naturally advantageous to use the amines in excess of the proportion theoretically required, i.e. in excess of the proportion required by whichever of the following equations is relevant:

(a) $PH_3 + RNH_2 = RPH_2 + NH_3$
(b) $PH_3 + \frac{1}{2}R_2NH = RPH_2 + \frac{1}{2}NH_3$
(c) $PH_3 + \frac{1}{3}R_3N = RPH_2 + \frac{1}{3}NH_3$
(d) $RPH_2 + RNH_2 = R_2PH + NH_3$
(e) $RPH_2 + \frac{1}{2}R_2NH = R_2PH + \frac{1}{2}NH_3$
(f) $RPH_2 + \frac{1}{3}R_3N = R_2PH + \frac{1}{3}NH_3$
(g) $R_2PH + PNH_2 = R_3P + NH_3$
(h) $R_2PH + \frac{1}{2}R_2NH = R_3p + \frac{1}{2}NH_3$
(i) $R_2PH + \frac{1}{3}R_3N = R_3p + \frac{1}{3}NH_3$ The excess of amine can be smaller with a secondary amine than with a primary amine, and smaller still with a tertiary amine, although it is possible to use the various amines in any desired mixing ratio for reaction with hydrogen phosphide.

The use of a slight excess of amine, and the adoption of a short contact time with the catalyst, will predominantly produce a low-alkylated product and will favour primary phosphines. The use of a large excess of amine, and the adoption of a long contact time, on the other hand, will predominantly produce a higher-alkylated phosphine, and will favour tertiary phosphines.

It is also possible, under appropriate operational conditions, to effect the following reactions:

(j) $PH_3 + R_3N = RPH_2 + R_2NH$
(k) $PH_3 + R_3N = R_2PH + RNH_2$
(l) $PH_3 + R_3N = R_3P + NH_3$
(m) $RPH_2 + R_3N = R_2PH + R_2NH$
(n) $RPH_2 + R_3N = R_3P + RNH_2$
(o) $R_2PH + R_3N = R_3P + R_2NH$ etc.

The reaction is preferably effected at atmospheric pressure or under the slightly superatmospheric pressure which is established on flowing the reactants through the reactor which provides the reaction zone.

The products coming from the reactor can be further processed by any of the usual procedures which are relevant. Thus the products can be separated from each other by distillation; or reaction gases containing products of different basicity can be scrubbed with an acid and these products separated via the resulting phosphonium salts. Unreacted starting materials can be recycled.

The process of the present invention, which is naturally not limited to the specific procedures described herein, permits the continuous commercial production of alkyl phosphines from readily accessible alkylamines and $PH_3$, $RPH_2$ or $R_2PH$, but especially $PH_3$, which is a by-product obtained in commercial quantities in inter alia the production of sodium hypophosphite. The alkyl phosphines obtained by the present process are of considerable interest as starting materials for the production of (e.g.) flameproofing agents and pharmaceutical preparations.

The following Examples illustrate the invention.

EXAMPLE 1: (General experimental conditions)

Methyl phosphines of the formulae $CH_3PH_2$, $(CH_3)_2PH$ and $(CH_3)_3P$ were prepared. To this end, 0.59 mol of $PH_3/h$ and 1.30 mols of $(CH_3)_3N/h$ were heated to 250° C. in a preheater and then contacted at 300° C., at atmospheric pressure and over a period of 64 seconds, with an active carbon catalyst (particle size = 0.5 to 2.0 mm) which had been placed in a fixed bed reactor.

Use was made of the different basicities of the reaction products which came out of the reactor to separate the three methylphosphines which were formed. Unreacted $PH_3$ and $(CH_3)_3N$ were recycled.

A $PH_3$-conversion rate of 90% was reached upon the first passage of the reaction mixture through the reactor. A total of 145 g of $PH_3$ was used. This gave:
138.2 g of $CH_3PH_2$ ≙ 67.5% $PH_3$-yield
72.2 g of $(CH_3)_2PH$ ≙ 27.3% $PH_3$-yield
8.1 g of $(CH_3)_3P$ ≙ 2.5% $PH_3$-yield
3.6 g of $P_4$ ≙ 2.7% $PH_3$-yield The separated methylphosphines had the following boiling points under 760 mm Hg:
$CH_3PH_2 = -15°$ C.
$(CH_3)_2PH = 10°-21°$ C.
$(CH_3)_3P = 38°-40°$ C.

The phosphines obtained were identified, in the form of their phosphonium chlorides, by NMR-spectroscopy (H- and P-resonances). The spectra were taken at 90 megahertz in a strong hydrochloric acid solution. The data indicated are rounded as they are slightly affected by the HCl concentration.

| | | | | | | | |
|---|---|---|---|---|---|---|---|
| $[CH_3PH_3]Cl$ | $\delta CH_3$ | 2,1 | $\tau CH_3$—P | 17 Hz | | | |
| | $\delta PH$ | 7,5 | $\tau P$—H | 555 Hz | $\tau PH$—$CH_3$ | 5 Hz | $\delta P+$ 62 |
| $[(CH_3)_2PH_2]Cl$ | $\delta CH_3$ | 2,0 | $\tau CH_3$—P | 16 Hz | | | |
| | $\delta PH$ | 6,5 | $\tau P$—H | 528 Hz | | | $\delta P+$ 31 |
| $[(CH_3)_3PH]Cl$ | $\delta CH_3$ | 1,95 | $\tau CH_3$—P | 15 Hz | $\tau CH_3$—PH | 5,5 Hz | |

| | | -continued | | |
|---|---|---|---|---|
| δPH | 6,4 | τP—H 507 Hz | | δP+ 3 |

EXAMPLE 2

CH$_3$PH$_2$ was prepared as the principal product. To this end, 0.66 mol/h of PH$_3$ and 1.21 mols/h of (CH$_3$)$_3$N were contacted for 11 seconds at 320° C. with an active carbon catalyst. The other conditions were as in Example 1. The PH$_3$-conversion rate was 61%; unreacted PH$_3$ was recycled. A total of 145 g of PH$_3$ was used. This gave
182.6 g of CH$_3$PH$_2$ ≙ 89.2% PH$_3$-yield
18.2 g of (CH$_3$)$_2$PH ≙ 6.9% PH$_3$-yield
1.6 g of (CH$_3$)$_3$P ≙ 0.5% PH$_3$-yield
4.5 g of P$_4$ ≙ 3.4% PH$_3$-yield The short contact time of 11 seconds thus produced predominantly the monoalkyl phosphine. This is also shown in the following Example.

EXAMPLE 3

CH$_3$PH$_2$ was produced as the principal product. To this end, 0.61 mol/h of PH$_3$ and 1.22 mols/h of (CH$_3$)$_3$N were contacted for 8 seconds at 310° C. with an active carbon catalyst. The other experimental conditions were as in Example 1.

The PH$_3$-conversion rate was 42%, unreacted PH$_3$ being recycled. 150 g PH$_3$ gave:
195.5 g of CH$_3$PH$_2$ ≙ 92.3% PH$_3$-yield
13.7 g of (CH$_3$)$_2$PH ≙ 5.0% PH$_3$-yield
0.7 g of (CH$_3$)$_3$P ≙ 0.2% PH$_3$-yield
3.4 g of P$_4$ ≙ 2.5% PH$_3$-yield

EXAMPLE 4

CH$_3$PH$_2$ was again prepared as the principal product. To this end, 2.13 mols/h of PH$_3$ and 0.49 mol/h of (CH$_3$)$_3$N were contacted for 19 seconds at 280° C. with an active carbon catalyst. The other experimental conditions were as in Example 1.

The PH$_3$-conversion rate was 39%, unreacted PH$_3$ being recycled. 134 g of PH$_3$ gave
170.4 g of CH$_3$PH$_2$ ≙ 90.1% of PH$_3$-yield
5.7 g of (CH$_3$)$_2$PH ≙ 2.4% of PH$_3$-yield
- (CH$_3$)$_3$P ≙ 0%
9.2 g of P$_4$ ≙ 7.5% of PH$_3$-yield Molar ratios of PH$_3$:alkyl amine greater than 1:1 were also % to favour the formation of monoalkyl phosphines.

EXAMPLE 5

(CH$_3$)$_2$PH and (CH$_3$)$_3$P were prepared as the principal products. To this end, 0.42 mol/h of PH$_3$ and 3.91 mols/h of (CH$_3$)$_3$N were contacted for 393 seconds at 320° C. with an active carbon catalyst. The other conditions were as described in Example 1.

The PH$_3$-conversion rate was 98% and 119 g of PH$_3$ gave:
22.0 g of CH$_3$PH$_2$ ≙ 13.1% of PH$_3$-yield
104.8 g of (CH$_3$)$_2$PH ≙ 48.3% of PH$_3$-yield
102.1 g of (CH$_3$)$_3$P ≙ 38.4% of PH$_3$-yield
0.2 g of P$_4$ ≙ 0.2% of PH$_3$-yield Long contact times thus produce predominantly di- and trialkylphosphines.

EXAMPLE 6

0.54 mol/h of PH$_3$ and 1.92 mols/h of (CH$_3$)$_3$N were contacted for 0.5 second at 300 ° C. with an active carbon catalyst.

The other conditions were as in Example 1.

The PH$_3$-conversion rate was 7%; unreacted PH$_3$ was recycled. 102 g of PH$_3$ gave:
137.1 g of CH$_3$PH$_2$ ≙ 95.2% of PH$_3$-yield
4.3 g of (CH$_3$)$_2$PH ≙ 2.3% of PH$_3$-yield
- (CH$_3$)$_3$P -
2.3 g of P$_4$ ≙ 2.5% of PH$_3$-yield

EXAMPLE 7

0.50 mol/h of PH$_3$ and 1.41 mols per hour of (CH$_3$)$_3$N were preheated to 200° C. and contacted for 61 seconds at 200° C. with an active carbon catalyst. The other conditions were as in Example 1.

The PH$_3$-conversion rate was 6%; unreacted PH$_3$ was recycled. 140 g of PH$_3$ gave:
168.8 g of CH$_3$PH$_2$ ≙ 85.4% of PH$_3$-yield
31.4 g of (CH$_3$)$_2$PH ≙ 12.31% of PH$_3$-yield
5.0 g of (CH$_3$)$_3$P ≙ 1.6% of PH$_3$-yield
1.5 g of P$_4$ ≙ 1.2% of PH$_3$-yield

EXAMPLE 8

0.63 mol/h of PH$_3$ and 1.03 mols/h of (CH$_3$)$_3$N were preheated to 350° C. and contacted for 5 seconds at 400° C. with an active carbon catalyst. The other conditions were as in Example 1.

The PH$_3$-conversion rate was 87%; unreacted PH$_3$ was recycled. 160 g of PH$_3$ gave
75.4 g of CH$_3$PH$_2$ ≙ 33.4% of PH$_3$-yield
82.0 g of (CH$_3$)$_2$PH ≙ 28.1% of PH$_3$-yield
52.6 g of (CH$_3$)$_3$P ≙ 14.7% of PH$_3$-yield
34.7 g of P$_4$ ≙ 23.8% of PH$_3$-yield A comparison with Example 7 shows that the di- and trialkyl phosphines tend to be formed in higher proportions at higher temperatures.

EXAMPLE 9: (Alkylation with a secondary alkylamine)

0.58 mol/h of PH$_3$ and 1.07 mol/h of (CH$_3$)$_2$NH were contacted for 11 seconds at 300° C. with an active carbon catalyst. The other conditions were as in Example 1.

The PH$_3$-conversion rate was 35%; unreacted PH$_3$ was recycled. 137 g of PH$_3$ gave
170.0 g of CH$_3$PH$_2$ ≙ 87.9% of PH$_3$-yield
8.7 g of (CH$_3$)$_2$PH ≙ 3.5% of PH$_3$-yield
- (CH$_3$)$_3$P -
10.7 g of P$_4$ ≙ 8.6% of PH$_3$-yield

EXAMPLE 10: (alkylation with a primary alkylamine)

0.59 mol/h of PH$_3$ and 1.18 mols/h of CH$_3$NH$_2$ were contacted for 10 seconds at 300° C. with an active carbon catalyst. The other conditions were as in Example 1.

The PH$_3$-conversion rate was 15%; unreacted PH$_3$ was recycled. 121 g of PH$_3$ gave:

142.6 g of $CH_3PH_2 \triangleq 83.5\%$ of $PH_3$-yield
3.8 g of $(CH_3)_2PH \triangleq 1.7\%$ of $PH_3$-yield
- $(CH_3)_3P$ -
16.3 g of $P_4 \triangleq 14.8\%$ of $PH_3$-yield

EXAMPLE 11

(Alkylation with a mixture of primary, secondary and tertiary alkylamines)

0.60 mol/h of $PH_3$ and an amine mixture comprising 0.31 mol/h of $(CH_3)_3N$, 0.42 mol/h of $(CH_3)_2NH$ and 0.38 mol/h of $CH_3NH_2$ were contacted for 11 seconds at 300° C. with an active carbon catalyst. The other conditions were as in Example 1.

The $PH_3$-conversion rate was 33%; unreacted $PH_3$ was recycled. 141 g of $PH_3$ gave:
170.8 g of $CH_3PH_2 \triangleq 85.8\%$ of $PH_3$-yield
8.7 g of $(CH_3)_2PH \triangleq 3.4\%$ of $PH_3$-yield
0.6 g of $(CH_3)_3P \triangleq 0.2\%$ of $PH_3$-yield
13.6 g of $P_4 \triangleq 10.6\%$ of $PH_3$-yield

EXAMPLE 12: (Copper catalyst)

0.63 mol/h of $PH_3$ and 1.25 mols/h of $(CH_3)_3N$ were contacted for 12 seconds at 350° C. with a catalyst. The catalyst was Cu metal in finely divided form which was deposited on aluminum silicate particles (size = 0.5 to 2.0 mm). The catalyst lost its red copper coloration immediately after the start of the reaction and became black. Photographs taken with a microprobe suggested that in this form the Cu was no longer present as free metal but was present, as a result of a reaction with the $PH_3$, in the form of a Cu phosphide which evidently had catalytic activity.

The other conditions were as in Example 1.

The $PH_3$-conversion rate was 56%; unreacted $PH_3$ was recycled. 152 g of $PH_3$ gave:
165.2 g of $CH_3PH_2 \triangleq 77.0\%$ of $PH_3$-yield
7.5 g of $(CH_3)_2PH \triangleq 2.7\%$ of $PH_3$-yield
- $(CH_3)_3P$ -
28.1 g of $P_4 \triangleq 20.3\%$ of $PH_3$-yield

EXAMPLE 13: (Nickel catalyst)

0.68 mol/h of $PH_3$ and 1.31 mols/h of $(CH_3)_3N$ were contacted for 11 seconds at 350° C. with a catalyst. The catalyst was finely distributed Ni metal which was deposited on $SiO_2$ particles (size = 0.5 to 2.0 mm). Here again, the Ni appeared to be converted to Ni phosphide at the start of the reaction.

The other conditions were as in Example 1.

The $PH_3$-conversion rate was 59%; unreacted $PH_3$ was recycled. 140 g of $PH_3$ gave:
133.8 g of $CH_3PH_2 \triangleq 67.7\%$ of $PH_3$-yield
11.0 g of $(CH_3)_2PH \triangleq 4.3\%$ of $PH_3$-yield
3.4 g of $(CH_3)_3P \triangleq 1.1\%$ of $PH_3$-yield
34.3 g of $P_4 \triangleq 26.9\%$ of $PH_3$-yield

EXAMPLE 14: (Iron catalyst)

0.67 mol/h of $PH_3$ and 1.29 mols/h of $(CH_3)_3N$ were contacted for 12 seconds at 350° C. with a catalyst. The catalyst was finely distributed Fe metal deposited on $Al_2O_3$ particles (size = 0.5 to 2.0 mm). Here again, the Fe appeared to be converted to Fe phosphide at the start of the reaction.

The other conditions were as in Example 1.

The $PH_3$-conversion rate was 21%; unreacted $PH_3$ was recycled. 125 g of $PH_3$ gave:
118.8 g of $CH_3PH_2 \triangleq 67.3\%$ of $PH_3$-yield
8.4 g of $(CH_3)_2PH \triangleq 3.7\%$ of $PH_3$-yield
- $(CH_3)_3P$ -
33.1 g of $P_4 \triangleq 29.0\%$ of $PH_3$-yield

EXAMPLE 15: (Use of a platinum-palladium mixture as catalyst)

0.50 mol/h of $PH_3$ and 1.17 mols/h of $(CH_3)_3N$ were contacted for 8 seconds at 310° C. with a catalyst. This catalyst was prepared by applying a mixture of Pt and Pd metals in finely divided form to an active carbon catalyst (particle size = 0.5 to 2.0 mm). There was reason to believe that the Pt and Pd metals were converted to Pt phosphide and Pd phosphide, respectively, at the start of the reaction.

The other conditions were as in Example 1.

The $PH_3$-conversion rate was 63%; unreacted $PH_3$ was recycled. 174 g of $PH_3$ gave:
159.5 g of $CH_3PH_2 \triangleq 81.3\%$ of $PH_3$-yield
19.5 g of $(CH_3)_2PH \triangleq 7.7\%$ of $PH_3$-yield
6.5 g of $(CH_3)_3P \triangleq 2.1\%$ of $PH_3$-yield
11.3 g of $P_4 \triangleq 8.9\%$ of $PH_3$-yield

EXAMPLE 16: (Fluidized bed technique)

0.92 mol/h of $PH_3$ and 1.94 mols/h of $(CH_3)_3N$ were contacted for 8 seconds at 350° C. with a fluidized bed catalyst. This catalyst was Cu metal applied in finely divided form on to $SiO_2$. The catalyst lost its metallic red copper coloration at the start of the reaction and became black (Cu phosphide may be assumed to have been formed). The other conditions were as in Example 1.

The $PH_3$-conversion rate was 37%; unreacted $PH_3$ was recycled. 230 g of $PH_3$ gave:
235.1 g of $CH_3PH_2 \triangleq 72.4\%$ of $PH_3$-yield
13.0 g of $(CH_3)_2PH \triangleq 3.1\%$ of $PH_3$-yield
- $(CH_3)_3P$ -
51.4 g of $P_4 \triangleq 24.5\%$ of $PH_3$-yield

EXAMPLE 17: (Fluidized bed technique)

0.98 mol/h of $PH_3$ and 2.07 mols/h of $(CH_3)_3N$ were contacted for 7 seconds at 350° C. with a fluidized bed catalyst. This catalyst was Ni metal applied in finely divided form to $SiO_2$. Here again, the Ni was assumed to have been converted to Ni phosphide at the start of the reaction. The other conditions were as in Example 1. The $PH_3$-conversion rate was 41%; unreacted $PH_3$ was recycled. 245 g of $PH_3$ gave:
217.6 g of $CH_3PH_2 \triangleq 62.9\%$ of $PH_3$-yield
22.3 g of $(CH_3)_2PH \triangleq 5.0\%$ of $PH_3$-yield
9.3 g of $(CH_3)_3P \triangleq 1.7\%$ of $PH_3$-yield
67.9 g of $P_4 \triangleq 30.4\%$ of $PH_3$-yield

EXAMPLE 18: (Alkylation of a primary phosphine)

0.57 mol/h of $CH_3PH_2$ and 0.86 mol per hour of $(CH_3)_3N$ were contacted for 25 seconds at 300° C. with an active carbon catalyst. The other conditions were as in Example 1.

The $CH_3PH_2$-conversion rate was 47%; unreacted $CH_3PH_2$ was recycled. 190 g of $CH_3PH_2$ gave:
156.8 g of $(CH_3)_2PH \triangleq 63.9\%$ of $CH_3PH_2$-yield
100.2 g of $(CH_3)_3P \triangleq 33.3\%$ of $CH_3PH_2$-yield
3.4 g of $P_4 \triangleq 2.8\%$ of $CH_3PH_2$-yield

EXAMPLE 19: (Alkylation of a secondary phosphine)

0.30 mol/h of (CH$_3$)$_2$PH and 1.14 mols/h of (CH$_3$)$_3$N were contacted for 17 seconds at 300° C. with an active carbon catalyst. The other conditions were as in Example 1.

The (CH$_3$)$_2$PH-conversion rate was 31%; unreacted (CH$_3$)$_2$PH was recycled. 130 g of (CH$_3$)$_2$PH gave:
157.0 g of (CH ) P - 98.5% of (CH$_3$)$_2$PH-yield
1.0 g of P - 1.5% of (CH$_3$)$_2$PH-yield

EXAMPLE 20

(Preparation of mono-ethyl phosphine)

0.48 mol/h of PH$_3$ and 0.64 mol/h of (C$_2$H$_5$)$_3$N were contacted for 18 seconds at 300° C. with an active carbon catalyst.

The other conditions were as in Example 1.

The reaction mixture was passed once over the catalyst and 40 g of monoethyl phosphine (C$_2$H$_5$PH$_2$) was obtained from 115 g of PH$_3$. This corresponded to a PH$_3$-conversion rate of 19.1%. The ethyl phosphine so obtained had a boiling point of 24° to 25° C. and was identified by NMR-spectroscopy, in the manner described in Example 1 for the methyl phosphines, as being ethyl phosphonium chloride (C$_2$H$_5$PH$_3$)Cl.

H-Resonances:
$\delta$CH$_3$ 1,4 CH$_3$—P 24 Hz $\nu$ CH$_3$-CH$_2$ 7 Hz
$\delta$CH$_2$ 2,5 CH$_2$—P 15 Hz
$\delta$Ph 7,25 P—H 525 Hz $\nu$ PH-CH$_2$ 4 Hz
P-resonances (based on H$_3$PO$_4$, 85% strength)
$\delta$p+51

EXAMPLE 21

(Preparation of mono-ethyl phosphine)

0.52 mol/h of PH$_3$ and 0.78 mol/h of (C$_2$H$_5$)$_3$N were contacted for 17 seconds at 350° C. with an active carbon catalyst. The other conditions were as in Example 1.

The starting mixture was passed once over the catalyst and 60 g of C$_2$H$_5$PH$_2$ was obtained from 120 g of PH$_3$. This corresponded to a PH$_3$-conversion rate of 27.4%.

EXAMPLE 22

(Preparation of mono-n-propyl phosphine)

0.35 mol/h of PH and 0.47 mol/h of (n-C$_3$H$_7$)$_3$N were contacted for 25 seconds at 320° C. with an active carbon catalyst. The other conditions were as in Example 1.

The starting mixture was passed once over the catalyst, and 38 g of mono-n-propyl phosphine was obtained from 97 g of PH$_3$. This corresponded to a PH$_3$-conversion rate of 17.5%.

The mono-n-propyl phosphine so obtained had a boiling point of 52 to 54° C., and it was identified by NMR-spectroscopy, in the manner described in Example 1 for the methyl phosphines, as being mono-n-propyl phosphonium chloride n-C$_3$H$_7$PH$_3$Cl.

H-Resonances:
$\delta$CH$_3$ 1,1 $\nu$ P—H 525 Hz
$\delta$CH$_2$ 1,7 p1 $\delta$CH$_2$ 2,3
$\delta$PH 7,4.

I claim:

1. A process for making an alkyl phosphine of the general formula:

$$R_nPH_{3-n} \qquad (I)$$

in which R stands for an alkyl group having 1 to 3 carbon atoms and n is a whole number of 1 to 3 which comprises reacting hydrogen phosphide, a primary phosphine of the formula RPH$_2$ or a secondary phosphine of the formula R$_2$PH with an alkylamine of the general formula:

$$R_nNH_{3-n} \qquad (II)$$

in which R and n have the meanings given above, in a molar ratio of 0.1 to 10 mols of the alkylamine of formula II per mol of hydrogen phosphide or primary or secondary phosphine; the reaction being effected at a temperature of 150° to 400° C., at atmospheric pressure up to a superatmospheric pressure of 1 atmosphere gauge, and with the exclusion of oxygen; a catalyst being employed comprising active carbon, copper (II) chromite, or one or more metals of Group Ib or VIII of the Periodic System of the elements, deposited individually or in combination on a catalyst carrier; and the starting materials being passed through a reaction zone at a rate which permits a contact time between them and the catalyst of 0.1 to 400 seconds.

2. The process as claimed in claim 1, wherein the reaction is effected at a temperature of 250° to 350° C.

3. The process as claimed in claim 1, wherein the reaction is effected in a fixed bed reactor.

4. The process as claimed in claim 3, wherein the catalyst has a particle size of 0.5 to 10 mm.

5. The process as claimed in claim 1, wherein the reaction is effected in a fluidized bed reactor.

6. The process as claimed in claim 5, wherein the catalyst has a particle size of 40 to 200 microns.

7. The process as claimed in claim 1, wherein the catalyst employed is an active carbon catalyst having a BET surface area of more than 10 m$^2$/g.

8. The process as claimed in claim 1, wherein the catalyst comprises one or more metals belonging to Group Ib or VIII of the Periodic System and the said metal(s) comprise(s) copper, iron, cobalt, nickel, rhodium, palladium, and platinum.

9. The process as claimed in claim 1, wherein the starting materials are intimately mixed together, heated to reaction temperature and then contacted with the catalyst.

10. The process as claimed in claim 1, wherein the starting materials are passed through the reaction zone at a rate which permits a contact time between them and the catalyst of 0.5 to 60 seconds.

* * * * *